United States Patent [19]

Von Burg

[11] Patent Number: 5,023,263
[45] Date of Patent: Jun. 11, 1991

[54] 42-OXORAPAMYCIN

[75] Inventor: Gregory F. Von Burg, Princeton, N.J.

[73] Assignee: American Home Products Corporation, New York, N.Y.

[21] Appl. No.: 564,910

[22] Filed: Aug. 9, 1990

[51] Int. Cl.$^5$ .................. A61K 31/395; C07D 491/16
[52] U.S. Cl. .................................. 514/291; 540/456; 546/90
[58] Field of Search ......................... 540/456; 546/90; 514/291

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,316,885 | 2/1982 | Rakhit | 424/122 |
| 4,401,653 | 4/1983 | Eng | 424/114 |
| 4,650,803 | 3/1987 | Stella et al. | 514/291 |
| 4,885,171 | 12/1989 | Surendra et al. | 424/122 |

OTHER PUBLICATIONS

J. Antibiot. 28, 721–726 (1975).
J. Antibiot. 28, 727–732 (1975).
J. Antibiot. 31, 539–545 (1978).
Can. J. Physiol. Pharmacol. 55, 48 (1977).
FASEB 3, 3411 (1989).
FASEB 3, 5256 (1989).
Lancet, 1183, (1978).
J. Am. Chem. Soc. 103, 3215 (1981).
Immunology, C.V. Moseby Co., pp. 12.8–12.11 (1989).

Primary Examiner—Robert T. Bond
Attorney, Agent, or Firm—Richard K. Jackson

[57] ABSTRACT

This invention provides an oxidized derivative of rapamycin in which the hydroxyl at the 42-position has been oxidized to the corresponding ketone or a pharmaceutically acceptable salt thereof, which by virtue of its immunosuppressive and antifungal activity is useful in treating transplantation rejection, host vs. graft disease, autoimmune diseases, diseases of inflammation, and fungal infections and a process for the preparation of this oxidized derivative of rapamycin.

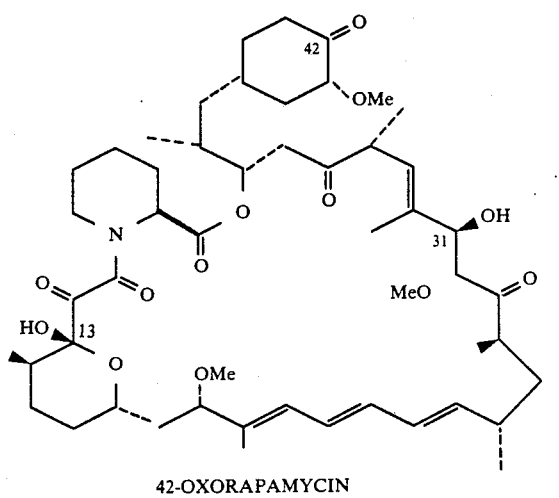

42-OXORAPAMYCIN

9 Claims, No Drawings

42-OXORAPAMYCIN

BACKGROUND OF THE INVENTION

This invention relates to an oxidized derivative of rapamycin, a process for its preparation, and a method for using it in the treatment of transplantation rejection, host vs. graft disease, autoimmune diseases, diseases of inflammation, and fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Seghal et al., J. Antibiot. 28, 727 (1975); H. A. Baker et al., J. Antibiot. 31, 539 (1978); U.S. Pat. Nos. 3,929,992; and 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989), rapamycin has been shown to be effective in inhibiting transplant rejection (U.S. patent application Ser. No. 362,544 filed Jun. 6, 1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to C. A. nomenclature, the esters described above would be at the 31- and 42-positions.

DESCRIPTION OF THE INVENTION

This invention provides a derivative of rapamycin which is useful as an antifungal agent possessing the general structure of rapamycin where the hydroxyl group in the 42-position has been oxidized to the corresponding ketone.

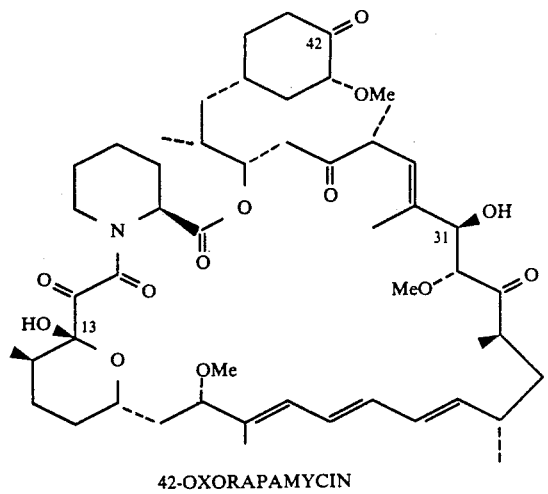

42-OXORAPAMYCIN

The pharmaceutically acceptable salts may be formed from inorganic cations such as sodium, potassium, and the like.

Although the oxidation of an alcohol to a ketone can be accomplished by numerous methods that have been described in the literature, this transformation is not trivial in polyhydroxylated macrocycles because functional group reactivity cannot readily be predicted [R. B. Woodward et al., J. Am. Chem. Soc. 103, 3215 (1981)]. As rapamycin has hydroxyl groups in the 13-, 31-, and 42-positions, the expected selectivity and reactivity problems were encountered. Numerous oxidative methods, including chromium, manganese, silver, iron, sulfur trioxide-pyridine, metachloroperbenzoic acid, and dimethylsulfoixde containing reagents failed to produce 42-oxorapamycin. To overcome these selectivity and reactivity problems, a process for the synthesis of 42-oxorapamycin using ruthenium-based reagents was developed.

Immunosuppressive activity was evaluated in an in vitro standard pharmacological test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from non-drug treated controls. The results are expressed by the following ratio:

$$\frac{^3H\text{-control thymus cells} - H^3\text{-rapamycin-treated thymus cells}}{^3H\text{-control thymus cells} - H^3\text{-test compound-treated cells}}$$

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient C3H mice. The drug is given daily, p.o. from Day 0 to Day 4. On Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg, p.o. gave 86% suppression, whereas cyclosporin A at the same dose gave 43% suppression. Results are expressed by the following ratio:

$$\frac{^3H\text{-}PLN \text{ cells control } C3H \text{ mouse} - ^3H\text{-}PLN \text{ cells rapamycin-treated } C3H \text{ mouse}}{^3H\text{-}PLN \text{ cells control } C3H \text{ mouse} - ^3H\text{-}PLN \text{ cells test compound-treated } C3H \text{ mouse}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28:385-402, (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days ±S.D.) of the drug treatment group is compared with the control group.

The following table summarizes the results of 42-oxorapamycin in these three standard test procedures.

TABLE 1

| Compound | LAF* (ratio) | PLN* (ratio) | Skin Graft (days + SD) |
|---|---|---|---|
| 42-oxorapamycin | 0.22 | −0.93 | 10.17 ± 0.41 |
| Rapamycin | 1.0 | 1.0 | 12.0 ± 1.7 |

*Calculation of ratios was described supra.

The results of these standard pharmacological test procedures demonstrate immunosuppressive activity both in vitro and in vivo for 42-oxorapamycin. A positive ratio in the LAF test procedure indicates suppression of T cell proliferation. As a transplanted pinch skin grafts are typically rejected within 6-7 days without the use of an immunosuppressive agent, the increased survival time of the skin graft when treated with 42-oxorapamycin further demonstrates its utility as immunosuppressive agents. While it appears that 42-oxorapamycin may cause T cell proliferation in the PLN test procedure, it is believed a negative ratio in this test procedure coupled with an increased survival time observed in the skin graft test procedure indicates a proliferation of T$_{suppressor}$ cells, which are implicated in suppressing the immune response. (see, I. Roitt et al. Immunology, C. V. Moseby Co. 1989, p 12.8-12.11).

Antifungal activity of 42-oxorapamycin and rapamycin was measured against 5 strains of *Candida albicans* using a plate assay for measurement of inhibition. The following represents the typical assay procedure used. Compound to be tested was placed on sterile dried ¼" plate disks, and allowed to dry. Agar plates were seeded with fungi and allowed to solidify. The impregnated disks were placed on the seeded Agar surface and incubated for the time required for the particular culture. Results are expressed in MIC (μg/ml) to inhibit growth.

TABLE 2*

| Compound | Strain of *Candida albicans* | | | | |
|---|---|---|---|---|---|
| | ATCC 10231 | ATCC 38246 | ATCC 38247 | ATCC 38248 | 3669 |
| 42-Oxorapamycin | 0.006 | 0.05 | 0.125 | 0.025 | 0.05 |
| Rapamycin | 0.003 | 0.025 | 0.003 | 0.006 | 0.025 |

*expressed as MIC (μg/ml)

Based on the results of these standard pharmacological test procedures, the compounds are useful in the treatment of transplantation rejection such as, heart, kidney, liver, bone marrow, and skin transplants; auto-immune diseases such as, lupus, rheumatoid arthritis, diabetes mellitus, myasthenia gravis, and multiple sclerosis; and diseases of inflammation such as, psoriasis, dermatitis, eczema, seborrhea, and inflammatory bowel disease; and fungal infections.

The compound claimed in this invention may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely devided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be appropriate number of any such compositions in package form. The dosage to be used in the treatment must be subjectively determined by the attending physician.

In addition, 42-oxorapamycin may be employed as a solution, cream or lotion by formulation with pharmaceutically acceptable vehicles containing 0.1–5 percent, preferably 2 percent of 42-oxorapamycin which may be administered to a fungally affected area.

The following examples illustrate the preparation of 42-oxorapamycin.

EXAMPLE 1

To 1.0 g of rapamycin in 10 ml of anhydrous dimethylformamide over 3A powdered molecular sieves was added 0.26 g (2.0 equivalents) of N-methyl morpholine, N-oxide followed by 60 mg of tris(triphenylphosphine) ruthenium dichloride. The reaction mixture was stirred at room temperature during which time oxidant and catalyst was added (0.26 g of oxidant and 60 mg of catalyst) every 8 hours for 48 hours. After 2 days at room temperature the reaction was diluted with ethyl acetate, filtered through Celite and the filtrate was evaporated. The residue containing 42-oxorapamycin and unreacted rapamycin was separated by reverse phase chromatography using a Dynamax column with 75% acetonitrile/water as mobile phase to give 0.25 g of rapamycin and 0.25 g of 42-oxorapamycin as an off-white solid; IR (KBr) 3425, 1720 cm$^{-1}$; $^1$H NMR (CDCl$_3$) $\delta$3.46 (3H, s), 3.35 (3H, s), 3.14 (3H, s), 1.75 (3H, s), 1.66 (3H, s), 1.26 (3H, s); $^{13}$C NMR 166.6, 169.23, 207.98; MS (negative ion FAB) 911 (M$^-$), 879, 590, 297, and 148.

EXAMPLE 2

To 1.0 g of rapamycin in 30 mL of dichloromethane over 3A powdered molecular sieves waqs added 1.0 g of ruthenium (IV) oxide monohydrate. The reaction mixture was stirred at 80° C. overnight. Additional ruthenium (IV) oxide (0.50 g) was added on day two and again on day three until the majority of the starting material had been consumed. On day four the reaction mixture was diluted with ethyl acetate and filtered through Celite. The filtrate was evaporated to give a yellow oil. Separation of unreacted repamycin from 42-oxorapamycin was accomplished by reverse phase chromatography using a Dynamax column and 75% acetonitrile/water as the mobile phase. This separation afforded 100 mg of unreacted rapamycin and 100 mg of 42-oxorapamycin as an off-white solid: MS (negative ion FAB) 911.

EXAMPLE 3

To a solution of 10 g (11 mmol) of rapamycin in 200 ml of acetonitrile was added 3.8 g (3 equivalents) of N-methyl morpholine N-oxide and then 193 mg (0.55 mmol, 0.05 equivalents) of tetra-n-propylammonium perruthenate. Additional perruthenate (193 mg) was added after 15 min and after 2 hours. One hour after the last addition, the acetonitrile was removed in vacuo and the residue was filtered through 60–200 mesh silica gel using ethyl acetate as eluting solvent. Flash chromatography on 60–200 mesh silica gel using hexane/ethyl acetate as the eluant gave after trituration with ethyl ether, 740 mg of 42-oxorapamycin and 820 mg of rapamycin.

Residual fractions containing primarily rapamycin and 42-oxorapamycin were combined and reoxidized two times (sequentially) to give crude title compound. Gravity chromatography on 60–200 silica gel using ethyl acetate as the eluant gave an additional 1.0 g of 42-oxorapamycin after removal of solvent from the appropriate fractions and trituration with ethyl ether. mp 200°–205° C.

Anal. Calcd.: C, 67.15; H, 8.51; N, 1.54. Found: C, 66.90; H, 8.32; N, 1.65.

What is claimed is:

1. 42-Oxorapamycin or a pharmaceutically acceptable salt thereof.

2. A method of treating transplantation rejection, host vs. graft disease, autoimmune diseases, and diseases of inflammation in a mammal by administering an effective amount of 42-oxorapamycin or a pharmaceutically acceptable salt thereof.

3. A method of treating fungal infections by administering an effective amount of 42-oxorapamycin or a pharmaceutically acceptable salt thereof.

4. A process for making 42-oxorapamycin from rapamycin using a ruthenium catalyst as an oxidant.

5. A process according to claim 4 using tris(triphenylphosphine)ruthenium as the oxidant.

6. A process according to claim 4 using ruthenium (IV) oxide as the oxidant.

7. A process according to claim 4 using tetra-n-propylammonium perruthenate as the oxidant.

8. A pharmaceutical composition comprising a compound of claim 1 or a pharmaceutically acceptable salt and a pharmaceutically acceptable carrier.

9. A composition as claimed in claim 8 in unit dosage form.

* * * * *